United States Patent [19]

Etzweiler et al.

[11] Patent Number: 5,214,160
[45] Date of Patent: May 25, 1993

[54] ACETYL-TRI-AND-TETRAMETHYL-OCTAHYDRONAPHTHALENES AND FRAGRANCE COMPOSITIONS CONTAINING SAME

[75] Inventors: Franz Etzweiler, Greifensee; Daniel Helmlinger, Gockhausen; Cornelius Nussbaumer, Schwerzenbach; Mario Pesaro, Zurich, all of Switzerland

[73] Assignee: Givaudan Corporation, Clifton, N.J.

[21] Appl. No.: 951,053

[22] Filed: Sep. 25, 1992

Related U.S. Application Data

[62] Division of Ser. No. 708,662, May 31, 1991, Pat. No. 5,180,709.

[30] Foreign Application Priority Data

Jun. 2, 1990 [EP] European Pat. Off. ......... 90110519.7

[51] Int. Cl.$^5$ ............................................. C07D 311/04
[52] U.S. Cl. ..................................... 549/290; 560/126
[58] Field of Search .......................... 549/290; 560/123

[56] References Cited

U.S. PATENT DOCUMENTS

| | | | |
|---|---|---|---|
| 3,076,022 | 1/1963 | Kitchens | 512/17 |
| 3,850,963 | 11/1974 | Thoma et al. | 549/290 |
| 3,856,819 | 12/1974 | Deumens et al. | 549/290 |
| 3,929,677 | 12/1975 | Hall et al. | 512/17 |

FOREIGN PATENT DOCUMENTS

| | | | |
|---|---|---|---|
| 2408689 | 9/1974 | Fed. Rep. of Germany | 512/17 |
| 3023483 | 7/1982 | Fed. Rep. of Germany | 512/17 |

OTHER PUBLICATIONS

Mousseron-Canet et al, Chem. Abst., vol. 54, #2400H (1960).
Nozoe et al, Tetrahedron, vol. 27, pp. 6073-6081 (1971).
M. Mousseron-Canet et al., Bull. Soc. Chim. France, (1959) 601-6.
K. Ishii et al., Heyl. Chim. Acta, 67 (1984) 1175-83.
S. Schreiber et al., J. Org. Chem., 54 (1989) 9-10.

Primary Examiner—James H. Reamer
Attorney, Agent, or Firm—Robert F. Tavares; Linda A. Vag

[57] ABSTRACT

The invention concerns novel odorants of formula I wherein R is hydrogen or methyl.

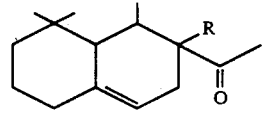

The invention also concerns fragrance compositions containing I.

Formula I is intended to particularly embrace as the racemates, (±)-3α-acetyl-3β,4β,5,5-tetramethyl-2,3,4,4aβ,5,6,7,8-octahydronapthalene and (±)-3α-acetyl-4β,5,5,-trimethyl-2,3β,4,4aβ,5,6,7,8-octahydronapthalene.

2 Claims, No Drawings

ACETYL-TRI-AND-TETRAMETHYL-OCTAHYDRONAPHTHALENES AND FRAGRANCE COMPOSITIONS CONTAINING SAME

This application is a division of application Ser. No.: 07/708,662 filed: May 31, 1991, U.S. Pat. No. 5,180,709 ACETYL-TRI-AND-TETRAMETHYL-OCTAHYDRONAPHTHALENES AND FRAGRANCE COMPOSITIONS CONTAINING SAME.

SUMMARY OF THE INVENTION

The invention concerns novel ordorants of formula I wherein R is hydrogen or methyl.

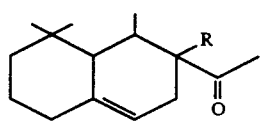

I

The invention also concerns fragrance compositions containing I.

Formula I is intended to particularly embrace the two enantiomers Ia and Ib as the racemates, namely (±)-3α-acetyl-3β,4β,5,5-tetramethyl-2,3,4,4aβ,5,6,7,8-octahydronapthalene and (±)-3α-acetyl-4β,5,5,-trimethyl-2,3β,4,4aβ,5,6,7,8-octahydronapthalene.

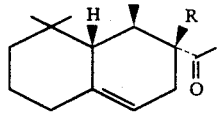

Ia

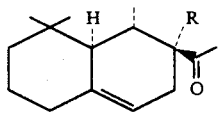

Ib

DESCRIPTION OF THE PREFERRED EMBODIMENTS

The invention also concerns a process for the manufacture of compounds of formula I, particulary compound Ia or Ib, and novel intermediates used in the process. The process comprises subjecting a compound of the formula

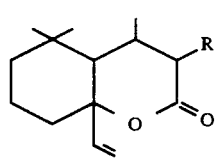

II wherein R is as above, preferably in the form of its corresponding silyl enol ether, to an Ireland-Claisen rearrangement, followed by a methylation of the 3 carboxyl group. This process can be represented as follows:

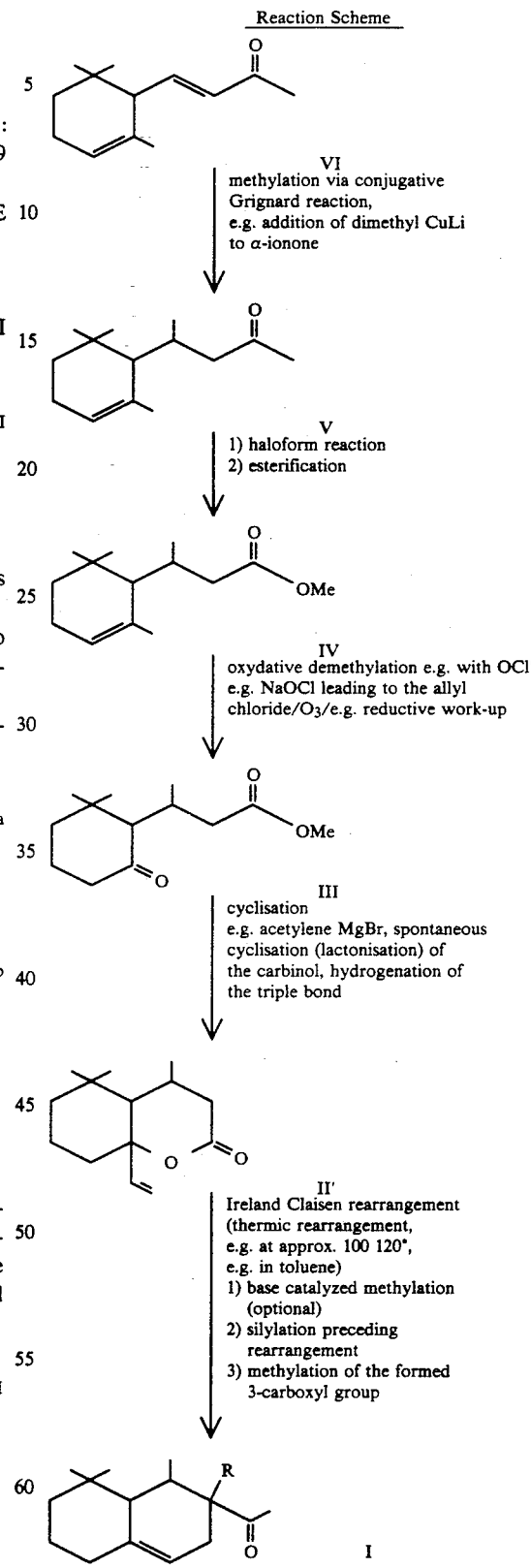

1) S. L. Schreiber et al., J. Org. Chem., 54 (1989) 9, 10

The individual steps involved in the process are based on chemistry known to one skilled in the art. The details of the methods are outlined in the Examples. It is a matter of course that modifications concerning the reagents and reaction conditions are possible. Such are embraced by the claims, since the originality of the access to, e.g. compound I resides in the selection of the various steps and its linkage together. As is shown by the Examples, reactions VI→V and III→II are stereoselective.

In the course of the present investigations it has been found that the novel compounds I possess valuable odorant properties and can accordingly be used as odorants. The olfactory notes of I can be characterized as follows: ambra, and also woody, flowery.

On the basis of their olfactory notes the compounds of formula I are especially suitable for modifying and intensifying known compositions. In particular, their extraordinary olfactory strength, which contributes quite generally to the refinement of the compositions, should be emphasized.

The tetramethyl derivative of I has been found to have the extraordinarily low threshold value of 5 pg/l air. In contradistinction thereto, the threshold value of the closely related 1,2,3,4,5,6,7,8-octahydro-2,3,8,8-tetra-methyl-2-acetonaphthone, Example 5 of DT-OS 2408689, has been determined to be 500 ng/l air, i.e., 100,000×the former value.

The compounds I combine with numerous known odorant ingredients of natural or synthetic origin, whereby the range of the natural odorants can embrace not only readily volatile, but also moderately-volatile and difficultly-volatile components, and that of the synthetics can embrace representatives from practically all classes of substances, as will be evident from the following compilation:

Natural products, such as tree moss absolute, basil oil, tropical fruit oils (such as bergamot oil, mandarin oil, etc.), mastix absolute, myrtle oil, palmarosa oil, patchouli oil, petitgrain oil, Paraguay, wormwood oil, alcohols, such as farnesol, geraniol, linalool, nerol, phenylethyl alcohol, rhodinol, cinnamic alcohol, Sandalore ® (Givaudan) (3-methyl-5-(2,2,3-trimethylcy-clopent-3-en-1-yl)pentan-2-ol), Sandela ® (Givaudan) (3-isocamphyl (5) cyclo-hexanol), aldehydes, such as citral, α-hexyl cinnamaldehyde, hydroxycitronellal, Lilial ® (Givaudan) (p-tert.butyl α-methyl dihydrocinnamaldehyde), methyl-nonylacetaldehyde, ketones, such as allylionone, α ionone, β ionone, isoraldein (isomethyl α ionone), methylionone, esters, such as allyl phenoxyacetate, benzyl salicylate, cinnamyl propionate, citronellyl acetate, citronellyl ethoxalate (citronellyl.O—CO—CO.OC$_2$H$_5$), decyl acetate, dimethylbenzylcarbinyl acetate, dimethylbenzylcarbinyl butyrate, ethyl acetoacetate, ethyl acetylacetate, hexenyl isobutyrate, linalyl acetate, methyl dihydrojasmonate, styrallyl acetate, vetiveryl acetate, (Givescone ™ (Givaudan) 2-ethyl 6,6 dimethyl (and 2,3,6,6 tetramethyl) 2 cyclohexene 1-carboxylic acid ethyl ester, Rosacetol ™ (Givaudan) (trichloromethyl benzyl acetate), Vetynal ® (Givaudan) (acetylated caryophyllene).

lactones, such as γ-undecalactone, various components often used in perfumery, such as musk ketone, indole, p-menthane-8-thiol-3-one, methyl eugenol, Further, the manner in which the compounds I round off and harmonize the olfactory notes of a wide range of known compositions without, however, dominating in an unpleasant manner is remarkable. There are to be mentioned in this connection: compositions with flowery, e.g. jasmine or rose, notes as well as woody, chypre, animalic, tobacco like and patchouli compositions, etc.

The compounds of formula I can be used in wide limits which can extend in compositions, for example, from about 0.1 (detergents)—about 5% (alcoholic solutions), without these values being, however, limiting values, since the experienced perfumer can also achieve effects with even lower concentrations or can synthesize novel complexes with even higher amounts. The preferred concentrations range between about 0.1% and about 3%. The compositions manufactured with I can be used for all kinds of perfumed consumer goods (eau de cologne, eau de toilette, extracts, lotions, creams, shampoos, soaps, salves, powders, toothpastes, mouth washes, deodorants, detergents, tobacco, etc.).

The compounds I can accordingly be used in the manufacture of compositions and, as the above compilation shows, a wide range of known odorants or odorant mixtures can be used. In the manufacture of such compositions the known odorants enumerated above can be used according to methods known to the perfumer, such as e.g. from W. A. Poucher, Perfumes, Cosmetics and Soaps 2, 7th edition, Chapman and Hall, London, 1974.

ILLUSTRATION OF THE PREFERRED EMBODIMENTS

Example 1

To a suspension of 91.1 g (0.48 mol) of CuI in 3 l of dry Et$_2$O were added at −10° 600 ml of 1.6M MeLi (0.96 mol) in Et$_2$O during 20 minutes. The mixture was stirred for 1 h at 0° and then cooled to −10°. A solution of 84.5 g (0.44 mol) of α ionone in 100 ml of Et$_2$O was added at −10° during 30 minutes and the resulting solution warmed up to room temperature. The reaction mixture was poured carefully on ice/water under N$_2$. The organic phase was separated, washed with brine, dried (MgSO$_4$) and evaporated. Distillation afforded 74.0 g (81%) of (4SR,1'SR)-4-(2',6',6'-trimethyl-2'-cyclohexen-1'-yl)pentan-2-one (1 diastereomer) (88% pure by GLC) as a colorless liquid.

bp.: 92°/0.4 Torr.

Odor: woody, floral (violet).

IR (CHCl$_3$): 1712 s.

MS: 208 (1, M+), 190(2), 150(51), 123(100), 85(57), 81(73), 43(94).

$^1$H-NMR (CDCl$_3$, 400 MH$_3$): 0.87 (s, CH$_3$); 0.99 (s, CH$_3$); 1.03 (d,J=7,CH$_3$); 1.07-1.15 (m,1H); 1.32-1.44 (m,2H); 1.70 (q,J=2,CH$_3$); 1.93-2.01 (m,2H); 2.11 (s,CH$_3$CO); 2.20 (dd,J=10.5 and 16.5, 1H); 2.35-2.45 (m,H C(4)); 2.51 (dd,J=3 and 16.5, 1H); 5.38 (m,w1/2=8, 1H).

Example 2

To a chilled (15°) solution of 37.0 g (0.18 mol) of (4SR,1'SR)-4-(2',6',6'-trimethyl-2'-cyclohexen-1'-yl)pentan-2-one in 700 ml of dioxane was added over a period of 15 minutes a cooled solution of NaOBr in H$_2$O (prepared by adding 40 ml of Br$_2$ to a solution of 124.3 g (3.11 mol) of NaOH in 1.1 l of H$_2$O). The resulting mixture was stirred at 15° for 1 h, and then at 25° for 2 h. 250 ml of 1M aq. Na$_2$SO$_3$ were added and the solvent evaporated under reduced pressure. The residue was distributed between H$_2$O and Et$_2$O. The aqueous layer was acidified with 200 ml of 25% H$_2$SO$_4$ and extracted with Et₂O. The organic phase was washed with brine, dried (MgSO₄) and concentrated in vacuo. Yield: 36.5 g of (3SR,1'SR)-3-(2',6',6'-trimethyl-2'-cyclohexen-1'-yl)butanoic acid, as a single diastereoisomer, m.p. 41°.

The crude acid was heated in 330 ml of benzene/MeOH 10:1 (v/v) with 2.0 g of p-TsOH for 8 h with azeotropic removal of H₂O. Work up afforded 36.2 g (91%) of (3SR,1'SR)-methyl-3-(2',6',6'-trimethyl-2'-cyclohexene-1'-yl)butyrate (82% pure, GLC).

Odor: woody, ionone like.

IR (CHCl₃): 1736s.

¹H-NMR (CDCl₃, 200 MHz): 0.87 (s,CH₃); 1.00 (s,CH₃); 1.04–1.60 (m,3H); overlapped by 1.09 (d,J=7,CH₃); 1.69 (q,J=2,CH₃); 1.90–2.06 (m,2H), overlapped by 2.04 (dd,J=10.5 and 14.5,1H); 2.22–2.40 (m,H C(3)); 2.43 (dd,J=3.5 and 14.5,1H); 3.65 (s,OCH₃); 5.37 (m,w1/2=8, 1H).

Example 3

To a chilled mixture of 31.1 g (0.14 mol) of (3SR,1'SR)-methyl-3-(2',6',6'-trimethyl-2'-cyclohexene-1'-yl)butyrate in 75 ml of hexane and 140 ml of 10% aqueous NaOCl were added during 20 minutes, 15 ml of 40% H₃PO₄ with cooling (pH 12.5→6.5). H₂O was then added and the product extracted with Et₂O. The organic extract was dried (MgSO₄) and concentrated in vacuo to give 31.1 g of a yellow liquid (82% pure by GLC).

¹H-NMR (CDCl₃, 200 MH₃): 4.54 (t,J=5,1H); 4.93 (br,s,1H); 5.33 (t,J=1,1H).

The crude allylchloride was dissolved in 700 ml of CH₃OH and cooled to −70°. Ozone, O₃, was bubbled through the solution until the starting material had disappeared. Excess of O₃ was removed by purging the solution with N₂, and the reaction mixture was poured into 100 g Zn/300 ml H₂O. The mixture was stirred at room temperature for 24 h, filtered and concentrated in vacuo. The residue was equilibrated between Et₂O and H₂O. Work up afforded 24.8 g of (3SR,1'SR)-methyl-3-(6',6'-dimethyl-2'-oxo-cyclohex-1'-yl)butyrate (64% GLC). An analytically pure sample was obtained by chromatography on SiO₂ with hexane/methyl tert.-butylether 10:1.

IR (CHCl₃): 1705s, 1735s.

MS: 226 (3,M+), 211(4), 195(6), 179(29), 153(24), 126(24). 111(100).

¹H-NMR (CDCl₃, 200 MHz): 0.97 (s,CH₃); 1.06 (d,J=6.5,CH₃); 1.12 (s,CH₃); 1.52–2.70 (m,10H); 3.67 (s,OCH₃).

Example 4

To a solution of acetylene magnesium bromide (0.1 mol) in 100 ml of THF was added, at 0°, over a period of 15 minutes a solution of 8.0 g (35 mmol) of (3SR,1'SR)-methyl-3 -(6',6'-dimethyl-2'-oxo-cyclohex-1'-yl)butyrate in 20 ml of THF during 15 minutes. The reaction mixture was warmed to room temperature during 4 h, poured into ice water/NH₄Cl and extracted with Et₂O to give 8.83 g of a red, viscous liquid. This lactone was dissolved in 150 ml of ethanol and hydrogenated at room temperature in the presence of 0.5 g of Lindlar's catalyst. Filtration and evaporation of the solvent, followed by chromatography on SiO₂ with hexane/methyl-tert.-butylether 9:1 afforded 3.8 g (48%) of crystalline (±)-3,4,4aβ,5,6,7,8a-octahydro-4β,5,5-trimethyl-8aβ-vinyl-coumarin, m.p. 84°–88° (from hexane).

IR (CHCl₃): 1730 cm⁻¹.

¹H-NMR (CDCl₃, 200 MH₃): 0.88 (s,CH₃); 0.94 (s,CH₃); 1.15 (d,J=7,CH₃); 1.16–1.96 (m,7H); 1.98–2.22 (m,1H); 2.31 (dd,J=9.5 and 16,1H); 2.54 (dd,J=8.5 and 16,1H); 5.13 (d,J=11,1H); 5.21 (d,J=17.5,1H); 5.94 (dd,J=11 and 17.5,1H).

Example 5

A solution of 2.22 g (10 mmol) of (±)-3,4,4aβ,5,6,7,8a-octahydro-4β,5,5-trimethyl-8aβ-vinyl-coumarin in 10 ml of THF was added at −70° to 30 ml of 0.37M (11 mmol) LDA (lithium diisopropylamide) (prepared from 20 ml of THF, 2 ml of diisopropylamine, 8 ml of 1.4M BuLi in hexane). The solution was stirred at 70°, then 0.75 ml (12 mmol) of CH₃I in 6 ml THF/DMPU 5:1 (v/v) were added. The solution was warmed up to 0°, cooled to −70° and treated with 10 ml of 1.4M BuLi in hexane. The mixture was stirred at −70° for 1 h, excess of trimethylchlorosilane was added and the solution warmed up to room temperature. The solvent was evaporated under reduced pressure, the residue taken up in hexane and filtered. The crude product was heated to reflux in 50 ml of toluene for 24 h. The solvent was stripped off, the residue dissolved in 50 ml of Et₂O and treated with 20 ml of 1.3M CH₃Li in Et₂O at 0°. The mixture was refluxed for 90 minutes, cooled and poured on 100 ml of cold 0.5N HCl with vigorous stirring. Work up, followed by chromatography on SiO₂ with hexane/ethylacetate (20:1) afforded 749 mg (32%) of (±)-3α-acetyl-3β,4β,5,5-tetramethyl-2,3,4,4aβ,5,6,7,8-octahydronaphthalene as a colorless oil.

IR (CHCl₃): 1700s.

MS: 234(23, M+), 219(7), 191(100).

¹H-NMR (CDCl₃, 400 MHz): 0.84 (s,CH₃); 0.89 (d,J=6.5,CH₃); 1.01 (s,CH₃); 1.05 (s,CH₃); 1.32–1.62 (m,5H); 1.71 (ddm,J=7/15/<1,1H); 1.80–1.92 (m,1H); 2.04–2.26 (m,6H), overlapped by 2.15 (s,CH₃CO); 5.44 (dq,J=7 and ~1,1H).

The proper stereostructure of (±)-3α-acetyl-3β,4β,5,5-tetramethyl-2,3,4,4aβ,5,6,7,8-octahydronaphthalene could unambiguously be assigned by ¹H/¹³C-shift correlated-2D-NMR, 2D-¹³C/¹³C-inadequate NMR and NOE difference spectroscopy.

Example 6

The procedure given for the preparation of (±)-3α-acetyl-3β,4β,5,5-tetramethyl-2,3,4,4aβ,5,6,7,8-octahydronaphthalene was followed, except that the initial methylation step was omitted.

Yield: 65% of (±)-3α-acetyl-4β,5,5-trimethyl-2,3β,4,4aβ,5,6,7,8-octahydronaphthalene as a colorless oil.

Odour: woody, amber, floral.

IR (CHCl₃): 1700s.

MS: 220 (9, M+·), 205(5), 177(28), 43(100).

¹H-NMR (CDCl₃, 400 MHz): 0.79 (s,CH₃); 0.98 (d,J=6.5,CH₃); 1.03 (s,CH₃); 1.34–2.23 (m,13H), overlapped by 2.17 (s,CH₃CO); 2.29 (td,J=11.5 and 4,H C(3)); 5.58 (dq,J=7 and <1H). Irradiation of the d at 0.98→dd at 1.97 (J=6.5 and 11.5,H C(4)).

Example 7

| | parts by weight | |
|---|---|---|
| a) Composition with flowery note | | |
| α-Phenyl ethyl acetate | 10.00 | 10.00 |

| -continued | parts by weight | |
|---|---|---|
| Geranyl acetate | 30.00 | 30.00 |
| Methyl isoeugenol | 10.00 | 10.00 |
| Geraniol | 50.00 | 50.00 |
| Hydroxycitronellal | 50.00 | 50.00 |
| Thibetolide TM (Givaudan) (ω-pentadecanolide) | 20.00 | 20.00 |
| Eugenol | 20.00 | 20.00 |
| Methyl dihydrojasmonate | 40.00 | 40.00 |
| 1,3,4,6,7,8-Hexahydro 4,6,6,7,8,8-hexamethyl cydopenta-γ-2-benzopyrane 50% DIP | 40.00 | 40.00 |
| Heliotropine | 20.00 | 20.00 |
| Benzyl acetate | 40.00 | 40.00 |
| Dimethyl benzyl carbinyl acetate | 40.00 | 40.00 |
| Cyclohexal | 40.00 | 40.00 |
| Musk ketone | 50.00 | 50.00 |
| γ-Methyl ionone | 80.00 | 80.00 |
| Phenyl ethyl alcohol | 100.00 | 100.00 |
| Benzyl salicylate | 100.00 | 100.00 |
| Bergamote essence | 100.00 | 100.00 |
| Dipropylene glycol | 80.00 | 160.00 |
| Compound of Example 5 | 80.00 | xxx |
| b) Composition with flowery note | | |
| 2,4-Dimethyl 3 cyclohexene 1 carboxaldehyde | 1.00 | 1.00 |
| Geranium ess. Bourbon | 5.00 | 5.00 |
| Eugenol | 5.00 | 5.00 |
| Vanilline 10%/DIP | 5.00 | 5.00 |

| -continued | parts by weight | |
|---|---|---|
| Indole 10%/DIP | 4.00 | 4.00 |
| Undecavertol TM (Givaudan) (4-methyl 3-dicen 5 ol) | 10.00 | 10.00 |
| Coumarine (pure crist.) | 10.00 | 10.00 |
| Patchouli ess. Indonesia | 20.00 | 20.00 |
| Amyl salicylate | 30.00 | 30.00 |
| Dihydromyrcenol | 60.00 | 60.00 |
| Methyl dihydrojasmonate | 60.00 | 60.00 |
| Sandalore ® (Givaudan) | 30.00 | 30.00 |
| Mandarine ess. | 50.00 | 50.00 |
| Methyl cedryl cetone | 100.00 | 100.00 |
| Fixolide ® (Givaudan) (7-acetyl-1,1,3,4,4,6-hexamethyltetralin | 100.00 | 100.00 |
|  | 100.00 | 100.00 |
| 1,3,4,6,7,8-Hexahydro 4,6,6,7,8,8-hexamethyl cydopenta-γ-2-benzopyrane 50% DIP | | |
| Bergamote essence | 200.00 | 200.00 |
| Lilial ® (Givaudan) | 60.00 | 60.00 |
| Dipropylene glycol | xxx | 150.00 |
| Compound of Example 5 | 150.00 | xxx |

The novel compound I provides richness and volume; it wraps up the synthetic notes and provides elegance.

We claim:
1. (3SR,1'SR)-Methyl-3-(6',6'-dimethyl-2'-oxo-cyclohex-1'-yl)butyrate.
2. (±)-3,4,4aβ,5,6,7,8a-Octahydro-4β,5,5-trimethyl 8aβ-vinyl-coumarin.

* * * * *